United States Patent

Kamachi et al.

[11] Patent Number: 4,457,929
[45] Date of Patent: Jul. 3, 1984

[54] 3-QUATERNARY AMMONIUM METHYL)-SUBSTITUTED CEPHALOSPORIN DERIVATIVES

[75] Inventors: Hajime Kamachi, Urayasu; Jun Okumura, Yokohama; Takayuki Naito, Kawasaki, all of Japan

[73] Assignee: Bristol-Myers Company, New York, N.Y.

[21] Appl. No.: 363,313

[22] Filed: Mar. 29, 1982

[51] Int. Cl.³ .................. A61K 31/545; C07D 501/46
[52] U.S. Cl. ...................................... 424/246; 544/22; 544/25
[58] Field of Search ..................... 424/246; 544/22, 25

[56] References Cited

U.S. PATENT DOCUMENTS 4,278,671 7/1981 Ochiai et al. .......................... 544/22
4,278,793 7/1981 Durckheimer et al. .............. 544/22

FOREIGN PATENT DOCUMENTS 1399086 6/1975 United Kingdom .
2040921 9/1980 United Kingdom .

Primary Examiner—Paul M. Coughlan, Jr.
Attorney, Agent, or Firm—Richard R. Lloyd

[57] ABSTRACT

Compounds of the formula

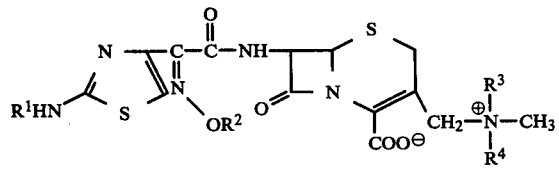

wherein $R^1$ is hydrogen or a conventional amino-protecting group, $R^2$ and $R^3$ each are independently methyl or ethyl, and $R^4$ is methyl, ethyl, n-propyl, isopropyl, n-butyl, isobutyl, allyl, 2-butenyl, 3-butenyl, 2-hydoxyethyl, 3-hydroxypropyl, 2-(dimethylamino)ethyl, pyridylmethyl, pyridylethyl, benzyl or phenethyl, and nontoxic pharmaceutically acceptable acid addition salts and solvates thereof, as well as processes for their preparation, are disclosed. The compounds in which $R^1$ is hydrogen are potent antibacterial agents.

11 Claims, No Drawings

3-QUATERNARY AMMONIUM METHYL)-SUBSTITUTED CEPHALOSPORIN DERIVATIVES

This is a continuation of application Ser. No. 931,419, filed Aug. 7, 1978 abandoned.

SUMMARY OF THE INVENTION

This invention relates to novel cephalosporin derivatives of the formula

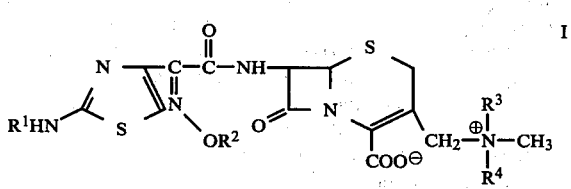

wherein $R^1$ is hydrogen or a conventional amino-protecting group, $R^2$ and $R^3$ each are independently methyl or ethyl, and $R^4$ is methyl, ethyl, n-propyl, isopropyl, n-butyl, isobutyl, allyl, 2-butenyl, 3-butenyl, 2-hydroxyethyl, 3-hydroxypropyl, 2-(dimethylamino)ethyl, pyridylmethyl, pyridylethyl, benzyl or phenethyl, and nontoxic pharmaceutically acceptable acid addition salts or solvates thereof. Processes for their preparation are also described.

DESCRIPTION OF THE PRIOR ART

U.K. Patent Specification No. 1,399,086 contains a generic disclosure encompassing a vast number of cephalosporins of the formula

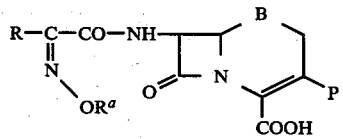

wherein R is hydrogen or an organic group, $R^a$ is an etherifying monovalent organic group linked to the oxygen through a carbon atom, B is $>S$ or $>S\to O$, and P is an organic group. However, the 2-aminothiazol-4-yl group is not identified as an R substituent and there are no examples in which P is a quaternary ammoniummethyl group of the type disclosed and claimed herein in the compounds of Formula I. U.S. Pat. No. 3,971,778 and its divisionals Nos. 4,024,133, 4,024,137, 4,064,346, 4,033,950, 4,079,178, 4,091,209, 4,092,477 and 4,093,803 have similar disclosures.

U.S. Pat. No. 4,278,793 contains a generic disclosure encompassing a vast number of cephalosporin derivatives of the formula

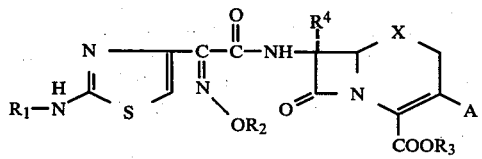

in which the variables $R_1$, $R_2$, $R_3$, $R_4$, X and A include generic definitions of the corresponding substituents of the compounds of Formula I claimed herein. However, in the 20 columns of definitions of the various substituent groups, the 78 page long table of structural formulae and the 225 examples, there is no disclosure that A may be a quaternary ammoniummethyl group of the type disclosed and claimed herein in the compounds of Formula I. United Kingdom Patent Specification No. 1,604,971 is concordant thereto and has a substantially identical disclosure. Published United Kingdom Patent Application No. 2,028,305 A, although apparently not formally related, contains the same broad generic disclosure but exemplifies A only as hydrogen.

U.S. Pat. No. 4,278,671 discloses 7-[2-(2-aminothiazol-4-yl)-2-(syn)-methoxyiminoacetamido]cephalosporin derivatives of the formula

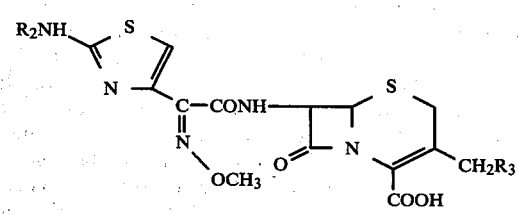

in which $R_2NH$ is an optionally protected amino group and $R_3$ is hydrogen or "the residue of a nucleophilic compound". The term "the residue of a nucleophilic compound" is broadly defined and it is then stated that $R^3$ "may alternatively be a quaternary ammonium group". Only pyridinium, variously substituted pyridinium, quinolinium, picolinium and lutidinium are disclosed as possible quaternary ammonium groups. There is no suggestion that the quaternary ammonium group may be of the type disclosed and claimed herein in the compounds of Formula I. United Kingdom Patent Specification No. 1,581,854 is concordant thereto and has a substantially identical disclosure. Other patents to the same patentee, which are not formally related but which have similar disclosures, include U.S. Pat. No. 4,098,888 and its divisionals U.S. Pat. Nos. 4,203,899, 4,205,180 and 4,298,606, and United Kingdom Patent Specification No. 1,536,281.

Published United Kingdom Patent Application No. 2,040,921 discloses cephalosporin derivatives of the formula

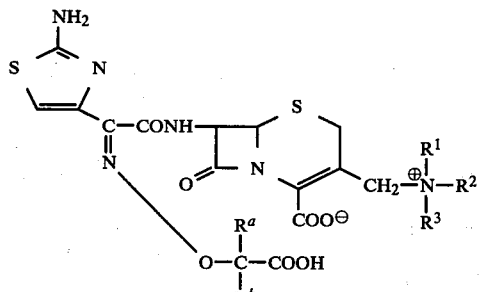

in which $R^a$ and $R^b$ are $C_{1-4}$ alkyl or, taken together with the carbon atom to which they are attached, form a $C_{3-7}$ cycloalkylidene ring, and $R^1$, $R^2$ and $R^3$ each are a $C_{1-4}$ alkyl group.

Complete Disclosure

This invention relates to cephalosporin derivatives of the formula

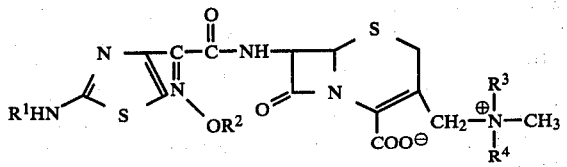

wherein $R^1$ is hydrogen or a conventional amino-protecting group, $R^2$ and $R^3$ each are independently methyl or ethyl, and $R^4$ is methyl, ethyl, n-propyl, isopropyl, n-butyl, isobutyl, allyl, 2-butenyl, 3-butenyl, 2-hydroxyethyl, 3-hydroxypropyl, 2-(dimethylamino)ethyl, pyridylmethyl, pyridylethyl, benzyl or phenethyl, and nontoxic pharmaceutically acceptable acid addition salts thereof, as well as processes for their preparation. Also included within the scope of this invention are the solvates (including hydrates) of the compounds of Formula I, as well as the tautomeric forms of the compounds of Formula I, e.g. the 2-iminothiazolin-4-yl form of the 2-aminothiazol-4-yl moiety.

As shown in the structural formula, the compounds of Formula I have the "syn" or "Z" configuration with respect to the alkoxyimino group. Because the compounds are geometric isomers, some of the "anti" isomer may also be present. This invention comprises compounds of Formula I containing at least 90% of the "syn" isomer. Preferably the compounds of Formula I are "syn" isomers which are essentially free of the corresponding "anti" isomers.

The nontoxic pharmaceutically acceptable acid addition salts of the compounds of Formula I include the salts with hydrochloric, hydrobromic, formic, nitric, sulfuric, methanesulfonic, phosphoric, acetic and trifluoroacetic acids, and other acids which have been used in the penicillin and cephalosporin art.

The compounds of Formula I in which $R^1$ is hydrogen exhibit high antibacterial activity against various Gram positive and Gram negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multi-dosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compound of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage of the compounds of Formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The preferred compounds of Formula I are those in which $R^1$ is hydrogen, $R^2$ is methyl, $R^3$ is methyl or ethyl, and $R^4$ is methyl, ethyl, 2-hydroxyethyl, 2-(dimethylamino)ethyl, allyl or pyridylmethyl. Particularly preferred compounds are those in which $R^1$ is hydrogen, $R^2$ and $R^3$ are methyl, and $R^4$ is methyl, 2-hydroxyethyl or allyl. The most preferred compound is that in which $R^1$ is hydrogen and $R^2$, $R^3$ and $R^4$ are methyl. In the primary evaluation of the preferred compounds of this invention, the Minimum Inhibitory Concentrations (MIC's) of the compounds were determined by the two-fold serial agar dilution method in Mueller-Hinton agar against 32 strains of test organisms in six groups. The geometric means of the MIC's determined in this test are shown in Table 1.

TABLE 1

| Compound of Example | Geometric Mean of MIC (mcg/mL) | | | | | |
|---|---|---|---|---|---|---|
| | (G+)-Ia (5 strains) | (G+)-Ib (5) | (G-)-Ia (5) | (G-)-Ib (6) | (G-)-II (5) | (G-)-III (6) |
| 1[a] | 1.1;1.6 | 3.6;3.6 | 0.033;0.029 | 0.25;0.20 | 0.69;0.69 | 3.2;4.0 |
| 2 | 1.6 | 4.7 | 0.038 | 0.18 | 0.60 | 3.5 |
| 3 | 1.4 | 3.6 | 0.044 | 0.22 | 0.69 | 5.6 |
| 4 | 2.1 | 4.7 | 0.057 | 0.22 | 0.69 | 7.1 |
| 8 | 2.1 | 5.5 | 0.087 | 0.50 | 1.4 | 7.9 |

(G+)-Ia: Penicillin-sensitive *S. aureus* (5 strains)
(G+)-Ib: Penicillin-resistant *S. aureus* (5 strains)
(G-)-Ia: Cephalothin-sensitive *E. coli* (2 strains), *Kl. pneumoniae* (1 strain) and *Pr. mirabilis* (2 strains)
(G-)-Ib: Cephalothin-resistant *E. coli* (3 strains) and *Kl. pneumoniae* (3 strains)
(G-)-II: *Pr. morganii* (1 strain), *Ent. cloacae* (2 strains) and *Ser. marcescens* (2 strains)
(G-)-III: *Ps. aeruginosa* (6 strains)
[a]Two different batches of Compound Ia The absorption of the most preferred Compound Ia (prepared in Example 1) was determined in mice following a single intramuscular injection of the test compound (dissolved in 0.1M phosphate buffer; pH 7) at a dosage of 20 mg/kg. Blood samples were collected from the orbital sinuses into heparinized capillary tubes and assayed in Mueller-Hinton medium using *Morganella morganii* A9695 as the test organism. The blood levels at various time intervals, the half-life values ($t_{\frac{1}{2}}$) and the areas under the curve (AUC) are shown in Table 2.

TABLE 2

| Mouse Blood Levels of Compound Ia | | |
|---|---|---|
| Blood levels | 10 | 14 |
| (mcg/mL) | 20 | 12 |
| at minutes | 30 | 8.8 |
| after | 40 | 7.5 |

TABLE 2-continued

| Mouse Blood Levels of Compound Ia | | |
|---|---|---|
| administration | 50 | 4.7 |
| | 60 | 4.4 |
| | 90 | 1.5 |
| | 120 | 0.74 |
| t½ (minutes) | 24 | |
| AUC mcg · hour/mL | | 10 |

The in vitro activity of the most preferred Compound Ia against 31 strains of fastidious bacteria was determined in GC agar, and the results are shown in Table 3.

TABLE 3

| In Vitro Activity of Compound Ia Against Fastidious Bacteria | |
|---|---|
| Test Organism | Geometric Mean of MIC (mcg/mL) |
| S. pyogenes (6 strains) | 0.013 |
| S. pneumoniae (6) | 0.013 |
| N. gonorrhoeae (4) | 0.013 |
| N. meningitidis (5) | 0.016 |
| H. influenzae (7) (ampicillin sensitive) | 0.013 |
| H. influenzae (3) (ampicillin resistant) | 0.20 |

In another aspect, this invention relates to processes for the preparation of the compounds of Formula I. There are two basic procedures for converting a readily available starting cephalosporin to another cephalosporin having different substituents on the 7- and 3-positions. One may first remove the 7-substituent and replace it with the desired 7-substituent, and then insert the desired 3-substituent. Alternatively, one may first insert the desired 3-substituent and subsequently exchange the 7-substituent. The compounds of Formula I may be prepared by either procedure and both are included within the scope of this invention, but it is preferred to insert the desired 7-substituent first and then insert the desired 3-substituent. The preferred procedure is shown below in Reaction Scheme 1 while the alternative procedure is shown in Reaction Scheme 2. The abbreviation "Tr" represents the trityl (triphenylmethyl) group, which is a preferred amino-protecting group. The abbreviation "Ph" represents the phenyl group. Thus, the —CH(Ph)$_2$ moiety is the benzhydryl group, which is a preferred carboxyl-protecting group.

Reaction Scheme 1

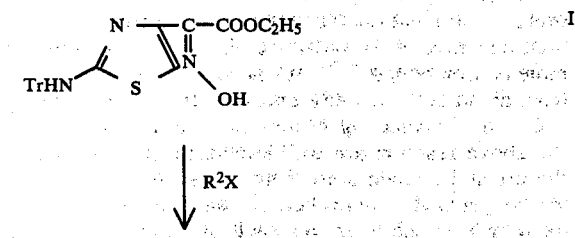

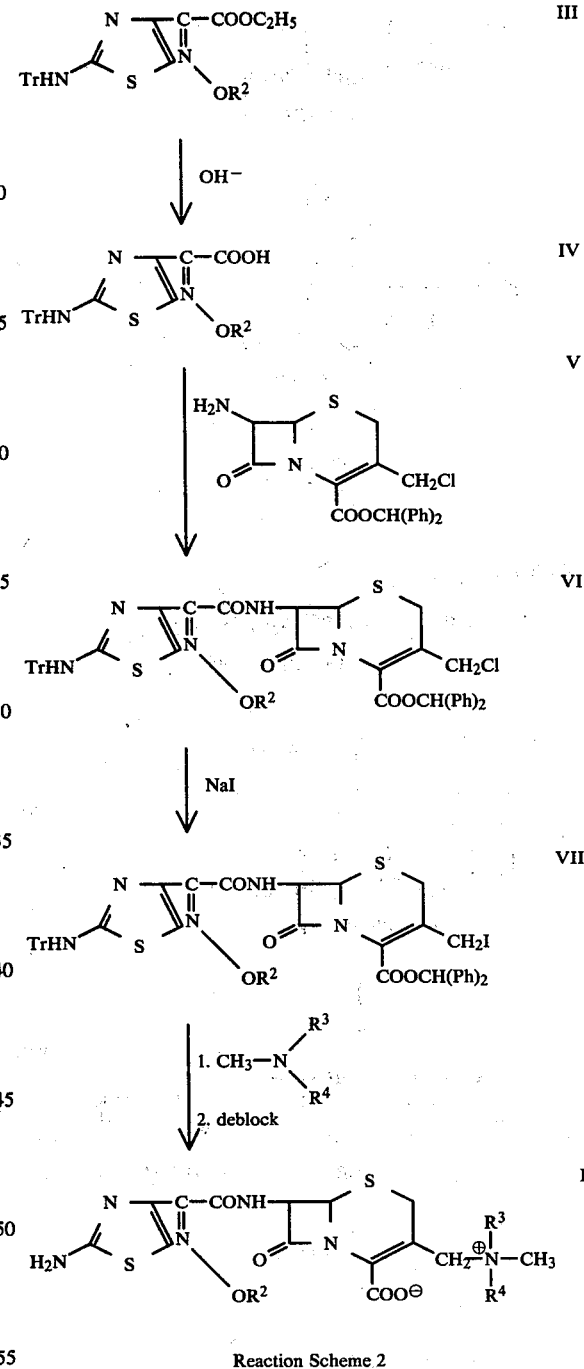

Reaction Scheme 2

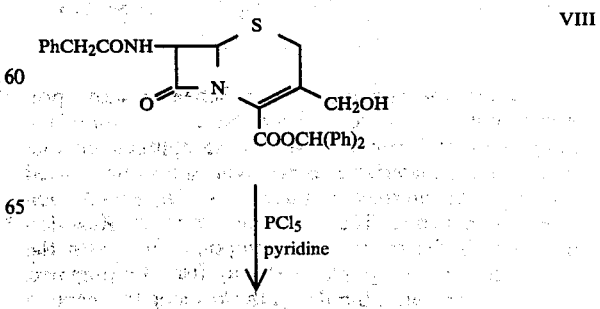

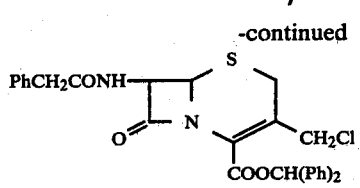

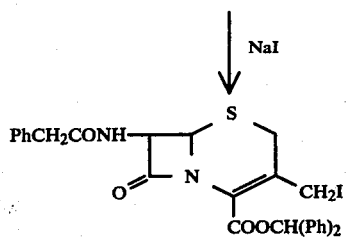

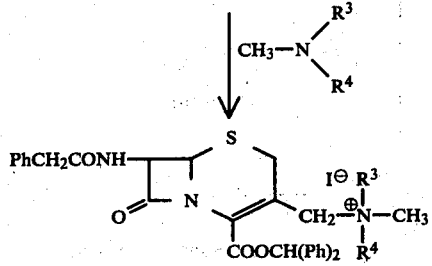

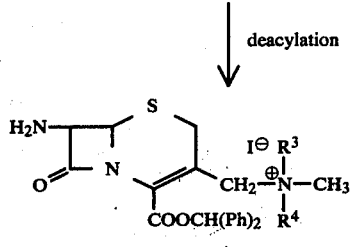

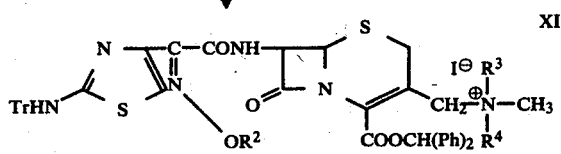

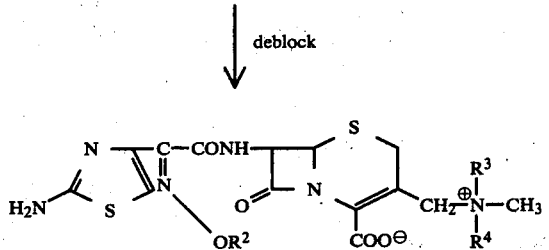

Although the above Reaction Schemes show preferred multi-step procedures for the preparation of the compounds of Formula I, it will be appreciated that other starting materials and procedures may be utilized to prepare the intermediates used in the key step of each Reaction Scheme. Thus, the key step in Reaction Scheme 1 is the reaction of Compound VII with the tertiary amine. Compound VII may itself be prepared by other procedures. Similarly, the key step in Reaction Scheme 2 is the acylation of Compound XII with Compound IV. Both compounds XII and IV may be prepared by other procedures.

The present invention provides a process for the preparation of compounds of the formula

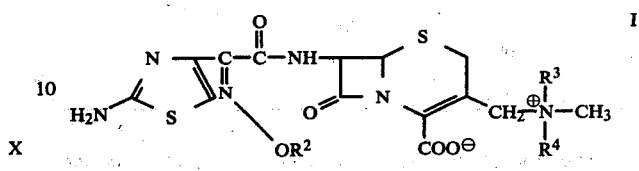

wherein $R^2$ and $R^3$ each are independently methyl or ethyl, and $R^4$ is methyl, ethyl, n-propyl, isopropyl, n-butyl, isobutyl, allyl, 2-butenyl, 3-butenyl, 2-hydroxyethyl, 3-hydroxypropyl, 2-(dimethylamino)ethyl, pyridylmethyl, pyridylethyl, benzyl or phenethyl, and non-toxic pharmaceutically acceptable salts and solvates thereof, which process comprises reacting a compound of the formula

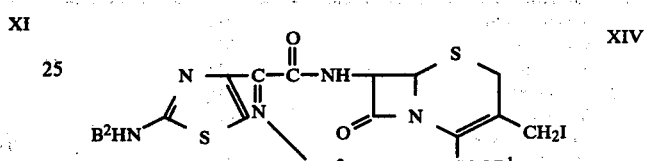

in which $R^2$ is as defined above, $B^1$ is a conventional carboxyl-protecting group and $B^2$ is a conventional amino-protecting group, with a tertiary amine of the formula

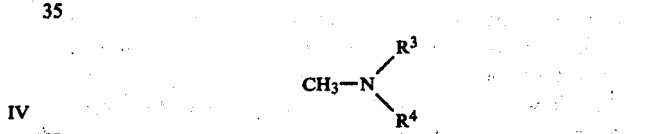

in which $R^3$ and $R^4$ are as defined above, to produce a compound of the formula

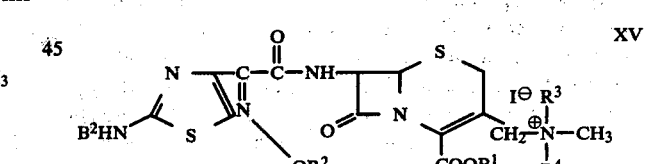

and subsequently removing all protecting groups by conventional means.

The reaction is carried out in a non-aqueous organic solvent such as methylene chloride, chloroform, ethyl ether, hexane ethyl acetate, tetrahydrofuran, acetonitrile and the like, or mixtures of such solvents. The reaction is conveniently carried out at a temperature of from about $-10°$ C. to about $+50°$ C., we normally prefer to conduct the reaction at room temperature. At least one mole of the tertiary amine should be used per mole of Compound XIV; we normally prefer to utilize from about 50% to 100% excess of the tertiary amine.

Carboxyl-protecting groups suitable for use as $B^1$ in the above reaction are well-known to those skilled in the art and include aralkyl groups such as benzyl, p-methoxybenzyl, p-nitrobenzyl and diphenylmethyl (benzhydryl); alkyl groups such as t-butyl; haloalkyl groups such as 2,2,2-trichloroethyl, and other carboxyl-protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as $B^2$ are also well-known in the art, and include the trityl group and acyl groups such as chloroacetyl. Amino-protecting groups which are readily removed by treatment with acid, e.g. the trityl group, are preferred.

The present invention also provides a process for the preparation of compounds of the formula

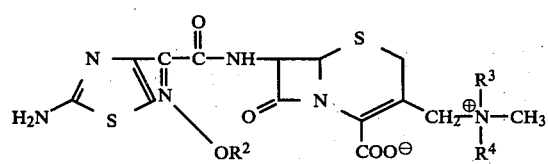

wherein $R^2$ and $R^3$ each are independently methyl or ethyl, and $R^4$ is methyl, ethyl, n-propyl, isopropyl, n-butyl, isobutyl, allyl, 2-butenyl, 3-butenyl, 2-hydroxyethyl, 3-hydroxypropyl, 2-(dimethylamino)ethyl, pyridylmethyl, pyridylethyl, benzyl or phenethyl, and non-toxic pharmaceutically acceptable salts and solvates thereof, which process comprises acylating a compound of the formula

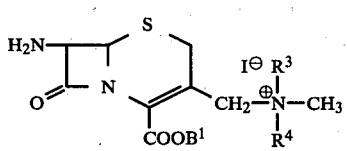

or an N-silyl derivative thereof, in which $B^1$ is hydrogen or a conventional carboxyl-protecting group and $R^3$ and $R^4$ are as defined above, with an acylating derivative of an acid of the formula

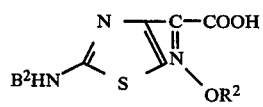

wherein $B^2$ is a conventional amino-protecting group and $R^2$ is as defined above, to produce a compound of the formula

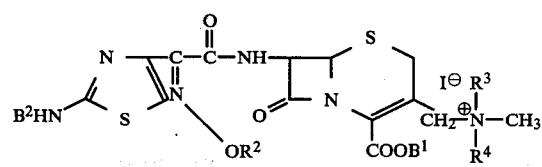

and subsequently removing all protecting groups.

The acylating derivatives of the acid of Formula XVII include the acid halides (and particularly the acid chloride), mixed acid anhydrides (such as the acid anhydrides formed with pivalic acid or a haloformate such as ethyl chloroformate), and activated esters (such as may be formed with N-hydroxybenztriazole in the presence of a condensing agent such as dicyclohexylcarbodiimide). The acylation may also be effected by use of the free acid of Formula XVII in the presence of a condensing agent such as dicyclohexylcarbodiimide, carbonyldiimidazole or an isoxazolium salt. As used herein, the term "acylating derivative" of the acid of Formula XVII includes the free acid itself in the presence of a condensing agent such as described above. The preferred acylating derivative of the acid of Formula XVII is the acid chloride, preferably used in the presence of an acid binding agent (and particularly a tertiary amine acid binding agent such as triethylamine, dimethylaniline or pyridine).

When the acylation is conducted with an acid halide it is possible to utilize an aqueous reaction medium, but a non-aqueous medium is preferred. When acid anhydrides, activated esters, or the free acid in the presence of a condensing agent, are used for the acylation, the reaction medium should be non-aqueous. Particularly preferred solvents for the acylation reaction are halogenated hydrocarbons such as methylene chloride and chloroform, but tertiary amides such as dimethylacetamide or dimethylformamide may be utilized, as well as other conventional solvents such as tetrahydrofuran, acetonitrile and the like.

The acylation reaction may be conducted at a temperature of from about $-50°$ C. to about $+50°$ C. However, it is preferably conducted at or below room temperature and most preferably from about $-30°$ C. to about $0°$ C. It is usually preferred to acylate the compound of Formula XVI with about a stoichiometric amount of the acylating agent of Formula XVII, although a small excess (e.g. 5-25%) of the acylating agent may be utilized.

It is preferable that the compound of Formula XVI be acylated in the form of its N-silyl derivative (when utilizing a non-aqueous reaction medium). This is conveniently done in situ by simply adding a suitable silylating agent (e.g. N,O-bistrimethylsilylacetamide) to the solution of Compound XVI prior to the addition of the acylating agent of Formula XVII. We prefer to utilize about 3 moles of silylating agent per mole of Compound XVI although this is not critical. The silyl compound is readily removed after acylation by the addition of water.

The tertiary amines of the formula

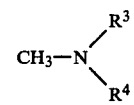

utilized in the preparation of the compounds of Formula I are commercially available or are readily prepared by methods known in the art.

PREPARATION NO. 1

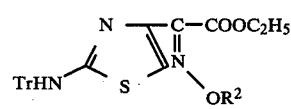

Ethyl (Z)-2-Methoxyimino-2-(2-tritylaminothiazol-4-yl)acetate (IIIa)

A mixture of ethyl (Z)-2-hydroxyimino-2-(2-tritylaminothiazol-4-yl)acetate (II) (5.00 g, 10.9 mmoles), CH₃I (2.04 mL, 32.8 mmoles) and K₂CO₃ (4.54 g, 32.8 mmoles) in dry dimethylsulfoxide (DMSO) (100 mL) was stirred at room temperature overnight and then poured into water (250 mL). The precipitate which formed was collected by filtration, washed with water and dried to give the title compound (5.15 g, quantitative yield). M.p. 115° C. (dec.).

NMR: $\delta^{CDCl_3}$ ppm 1.32 (3H, t), 3.98 (3H, s), 4.30 (2H, q), 6.42 (1H, s), 7.2 (1H, m), 7.25 (15H, s).

Compound IIIb was prepared by the general procedure set forth above, but replacing the methyl iodide with ethyl iodide.

| Compound | R² | Yield (%) | Mp (°C.) | Literature[1] Mp (°C.) |
|---|---|---|---|---|
| IIIa | methyl | 100 | 115° (dec.) | ca. 120° (dec.) |
| IIIb | ethyl | 67 | 97–98° | * |

*The ester was hydrolyzed without isolation
[1]Tetrahedron, 34, 2233 (1978)

PREPARATION NO. 2

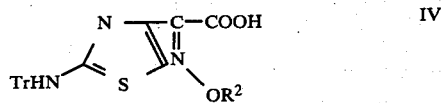

(Z)-2-Methoxyimino-2-(2-tritylaminothiazol-4-yl)acetic acid (IVa)

The ethyl ester IIIa prepared in Preparation No. 1 (6.00 g, 12.7 mmoles) in ethanol (120 mL) was treated with 2N NaOH (12.7 mL) at room temperature overnight. The reaction mixture was adjusted to pH 8 by the addition of powdered dry ice and the solvent was evaporated under reduced pressure. The residue was dissolved in water (100 mL) and the solution was acidified with 1N HCl to pH 2 and then extracted with ethyl acetate (3×50 mL). The combined extracts were washed with a saturated aqueous NaCl solution, dried and evaporated. The residue was crystallized from ethyl acetate-hexane to afford 5.56 g (yield 98%) of the title product. M.p. 138°–143° C. (dec.).

NMR: $\delta^{CDCl_3}$ ppm 3.89 (3H, s), 6.52 (1H, s), 7.2 (15H, s).

Compound IVb was prepared by the general procedure set forth above.

| Compound | R² | Yield (%) | Mp (°C., dec.) | Literature[1] Mp (°C., dec.) |
|---|---|---|---|---|
| IVa | methyl | 98 | 138–143 | ca. 140 |
| IVb | ethyl | 85 | 140–145 | not reported |

[1]Tetrahedron, 34, 2233 (1978)

PREPARATION NO. 3

Benzhydryl 3-Hydroxymethyl-7-phenylacetamido-3-cephem-4-carboxylate (VIII)

To a stirred suspension of phosphate buffer (pH 7, 162.5 mL) and wheat bran (20 g, dry) at room temperature was added 7-phenylacetamidocephalosporanic acid sodium salt (5 gm, 12.1 mmoles) in one portion. The progress of the reaction was monitored by HPLC until the hydrolysis was complete (5 hours). The suspension was filtered to remove the wheat bran and the filtrate was cooled to 5°–10° C. for extractive esterification. To the cooled solution was added methylene chloride (32 mL) followed by a 0.5M solution of diphenyldiazomethane in methylene chloride (24 mL). The pH was then adjusted to 3.0 with 28% phosphoric acid. After 1 hour the reaction mixture was allowed to rise to 20° C. Heptane (56 mL) was slowly added and the resulting crystalline title product was recovered by filtration. Yield of the title product was 3.0 gm (50%).

PREPARATION NO. 4

Benzhydryl 7-Amino-3-chloromethyl-3-cephem-4-carboxylate (V)

To a slurry of PCl₅ (8.3 g, 40 mmoles) in CH₂Cl₂ (100 mL) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate prepared in Preparation No. 3 (5.1 g, 10 mmoles) with stirring at −40° C., in one portion. The mixture was stirred at −10° C. for 15 minutes and allowed to stand at −10° C. to −15° C. for 7 hours. To the cooled solution (−20° C.) was added propane-1,3-diol (10 mL) and the mixture was allowed to stand at −20° C. for 16 hours and then at room temperature for 20 minutes with stirring. The resulting solution was washed with ice-water (2×20 mL) and saturated aqueous NaCl (10 mL), dried over MgSO₄ and concentrated in vacuo. The gummy residue (12 g) was dissolved in a mixture of CHCl₃ and n-hexane (2:1), and subjected to chromatography using a silica gel column (200 g) and the same solvent as eluant. Fractions containing the title compound were evaporated in vacuo and the residue triturated with n-hexane to give the title product (2.1 g, 51%), melting at >110° C. (dec.).

IR: $\nu_{KBr}$ 3400, 2800, 1785, 1725 cm⁻¹.

UV: $\lambda_{max}^{EtOH}$ 265 nm (E₁ cm¹% 160).

NMR: $\delta_{ppm}^{DMSO-d6+CDCl_3}$ 3.69 (2H, s), 4.43 (2H, s), 5.09 (1H, d, J=4.5 Hz), 5.24 (1H, d, J=4.5 Hz), 6.87 (1H, s), 7.3 (10H, m).

PREPARATION NO. 5

Benzhydryl 3-Chloromethyl-7-[(Z)-2-methoxyimino-2-(2-tritylaminothiazol-4-yl)acetamido]-3-cephem-4-carboxylate (VIa)

Benzhydryl 7-amino-3-chloromethyl-3-cephem-4-carboxylate prepared in Preparation No. 4 (2.29 g, 5.52 mmoles) in CH₃CN (57 mL) was treated with bis(trimethylsilyl)acetamide (BSA, 4.09 mL, 16.6 mmoles) at room temperature for 50 minutes to give a clear solution. To the solution was added an acid chloride solution, which was prepared from (Z)-2-methoxyimino-2-(2-tritylaminothiazol-4-yl)acetic acid (IVa) (2.04 g, 4.60 mmoles) and PCl₅ (1.15 g, 5.52 mmoles) in methylene chloride (20 mL). The mixture was stirred at room temperature for 30 minutes, poured into cold water (200 mL) and extracted with ethyl acetate (3×100 mL). The combined extracts were washed with aqueous NaCl, dried and evaporated. The residual syrup (4 g) was chromatographed on a silica gel (150 g) column by eluting with 10:1 and 3:1 mixtures of toluene and ethyl acetate successively. The fractions containing the desired compound were combined and evaporated to afford 2.61 g (68%) of VIa as an amorphous powder.

NMR: $\delta^{CDCl_3}$ ppm 3.50 (2H, s), 4.02 (3H, s), 4.33 (2H, s), 4.98 (1H, d), 5.87 (1H, q), 6.65 (1H, s), 6.90 (1H, s), 7.3 (25H, m).

PREPARATION NO. 6

Benzhydryl
3-Iodomethyl-7-[(Z)-2-methoxyimino-2-(2-tritylaminothiazol-4-yl)acetamido]-3-cephem-4-carboxylate (VIIa)

A mixture of the 3-chloromethyl derivative prepared in Preparation No. 5 (VIa) (1.50 g, 1.79 mmoles) and NaI (1.34 g, 8.93 mmoles) in methyl ethyl ketone (30 mL) was stirred at room temperature for 1 hour. After evaporation of the solvent the residue was dissolved in ethyl acetate (100 mL) and washed with water, aqueous $Na_2S_2O_3$ and aqueous NaCl, dried and evaporated to give the title compound VIIa (1.47 g, 89%) as an amorphous powder.

NMR: $\delta^{CDCl_3}$ ppm 3.55 (2H, ABq), 4.00 (3H, s), 4.25 (2H, s), 4.97 (1H, d), 5.80 (1H, q), 6.65 (1H, s), 6.90 (1H, s), 7.3 (25H, m).

PREPARATION NO. 7

Benzhydryl
3-Chloromethyl-7-[(Z)-2-ethoxyimino-2-(2-tritylaminothiazol-4-yl)acetamido]-3-cephem-4-carboxylate (VIb)

To a solution of (Z)-2-ethoxyimino-2-(2-tritylaminothiazol-4-yl)acetic acid (IVb) (1.095 g, 2.4 mmoles) in dichloromethane (20 mL) was added phosphorus pentachloride (500 mg). After stirring for 1 hour at room temperature, the mixture was added in one portion to an ice-cooled solution of Compound V (1.083 g, 2.4 mmoles) and BSA (1 mL) in dichloromethane (20 mL). After stirring for 0.5 hour the reaction mixture was poured into 10% aqueous $NaHCO_3$ (200 mL) and extracted with $CHCl_3$ (100 mL). The extract was washed with water, dried over $MgSO_4$, and evaporated under reduced pressure. The residue was chromatographed on a silica gel column. Elution with $CHCl_3$ gave VIb as an amorphous powder, 1.76 g (86%).

NMR: $\delta^{CDCl_3}$ ppm 1.40 (3H, t, $CH_2CH_3$), 3.53 (2H, ABq, 2—$CH_2$), 4.37 (2H, s, —$CH_2Cl$), 4.60 (2H, q, —$CH_2CH_3$), 4.90 (1H, d, 6—H), 5.89 (1H, d, 7—H), 6.88 (1H, s, thiazole—H), 6.91 (1H, s, benzhydryl—CH).

PREPARATION NO. 8

Diphenylmethyl
7-[(Z)-2-Ethoxyimino-2-(2-tritylaminothiazol-4-yl)acetamido]-3-iodomethyl-3-cephem-4-carboxylate (VIIb)

A mixture of VIb prepared in Preparation No. 7 (1.07 g, 1.25 mmoles) and NaI (562 mg, 2.75 mmoles) in acetone (20 mL) was stirred for 1 hour. The mixture was filtered and the filtrate was poured into water and extracted with ethyl acetate. The organic layer was washed successively with 5% aqueous $Na_2S_2O_3$, water and saturated aqueous NaCl, dried over $MgSO_4$ and evaporated to give 1.04 g (89%) of Compound VIIb.

NMR: $\delta^{CDCl_3}$ ppm 3.55 (2H, q, 2—$CH_2$), 4.27 (2H, s, $CH_2I$), 5.02 (1H, d, 6—H), 5.87 (1H, d, 7—H), 6.68 (1H, s, thiazole ring H), 6.93 (1H, s, benzhydryl—CH).

EXAMPLE 1

7-[(Z)-2-(2-Aminothiazol-4-yl)-2-methoxyiminoacetamido]-3-(trimethylammonium)methyl-3-cephem-4-carboxylate (Ia)

A 1M solution of trimethylamine in diethyl ether (1 mL; 1 mmole) was added to a stirred suspension of benzhydryl 3-iodomethyl-7-[(Z)-2-methoxyimino-2-(2-tritylaminothiazol-4-yl)acetamido]-3-cephem-4-carboxylate (VIIa) (468 mg; 0.5 mmole) in diethyl ether (30 mL) and the mixture was stirred for 1.5 hours. The precipitated quaternary salt (XVa) was collected by filtration (410 mg; 82% yield) and trifluoroacetic acid (TFA) (3 mL) was added. This mixture was stirred for 1.5 hours at room temperature and then evaporated to dryness under reduced pressure below 20° C. The residue was triturated with ether and the precipitated TFA salt was collected by filtration (yield 365 mg), dissolved in a small amount of methanol and chromatographed on a column of HP-20 resin (1.8×20 cm). The column was eluted with water (ca. 1 L) and then with 30% aqueous methanol (0.5 L). The methanolic eluate was evaporated under reduced pressure below 40° C. and the residue was freeze-dried to give the crude title product (yield 129 mg). The ratio of $\Delta^2/\Delta^3$ isomers in the crude product was 1:2, as determined by HPLC. The product was purified by HPLC (Lichrosorb RP-18, 8×300 mm, eluted with 1/100M $NH_4H_2PO_4$ (pH 7.2):$CH_3OH = 85:15$). The HPLC eluate was chromatographed on a column of HP-20 (1.8×15 cm) to remove the inorganic salt. The column was eluted with water (0.5 L) and then with 30% aqueous methanol (0.5 L). The methanolic eluate was evaporated under reduced pressure below 40° C. and the residue was freeze-dried to give the title compound (Ia) as an amorphous powder. Yield 75 mg (33%, based on VIIa). The product gradually decomposed above 160° C. Estimated purity 80%.

IR: $\nu_{max}^{KBr}$ cm$^{-1}$ 3600-3000, 1775, 1660, 1610, 1540, 1350, 1030.

UV: $\lambda_{max}^{phosphate\ buffer\ (1/15M,\ pH\ 7)}$ nm($\epsilon$) 235 (15700), 257 (15400).

NMR: $\delta^{D_2O}$ ppm 3.25 (9H, s, N+($CH_3$)$_3$), 4.10 (3H, s, $OCH_3$), 5.47 (1H, d, 4 Hz, 6—H), 5.96 (1H, d, 4 Hz, 7—H), 7.10 (1H, s, thiazole—H).

EXAMPLE 2

7-[(Z)-2-(2-Aminothiazol-4-yl)-2-methoxyiminoacetamido]-3-[N,N-dimethyl-N-(2-hydroxyethyl)ammonium]methyl-3-cephem-4-carboxylate (Ib)

The general procedure of Example 1 was repeated except that the trimethylamine utilized therein was replaced by an equimolar amount of N,N-dimethylethanolamine. The crude product had a $\Delta^2:\Delta^3$ ratio of 1:2. After purification the title compound was obtained in 17% yield and decomposed above 160° C. Estimated purity 90%.

EXAMPLE 3

7-[(Z)-2-(2-Aminothiazol-4-yl)-2-methoxyiminoacetamido]-3-(N,N-dimethyl-N-allylammonium)methyl-3-cephem-4-carboxylate (Ic)

The general procedure of Example 1 was repeated except that the trimethylamine utilized therein was replaced by an equimolar amount of N,N-dimethylallylamine. The crude product had a $\Delta^2:\Delta^3$ ratio of 1:4.5.

After purification the title compound was obtained in 14% yield and decomposed above 150° C. Estimated purity 80%.

EXAMPLE 4

7-[(Z)-2-(2-Aminothiazol-4-yl)-2-methoxyiminoacetamido]-3-[N,N-dimethyl-N-(3-pyridylmethyl)ammonium]methyl-3-cephem-4-carboxylate (Id)

The general procedure of Example 1 was repeated except that the trimethylamine utilized therein was replaced by an equimolar amount of 3-(dimethylaminomethyl)pyridine. The crude product had a $\Delta^2$:$\Delta^3$ ratio of 1:4.3. After purification the title compound was obtained in 17% yield and decomposed above 170° C. Estimated purity 75%.

EXAMPLE 5

7-[(Z)-2-(2-Aminothiazol-4-yl)-2-methoxyiminoacetamido]-3-[N,N-dimethyl-N-(2-dimethylaminoethyl)ammonium]methyl-3-cephem-4-carboxylate (Ie)

The general procedure of Example 1 was repeated except that the trimethylamine utilized therein was replaced by an equimolar amount of 1,2-bis(dimethylamino)ethane. The crude product had a $\Delta^2$:$\Delta^3$ ratio of 1:1. After purification the title compound was obtained in 14% yield and decomposed above 150° C. Estimated purity 65%.

EXAMPLE 6

7-[(Z)-2-(2-Aminothiazol-4-yl)-2-methoxyiminoacetamido]-3-(N,N-dimethyl-N-ethylammonium)methyl-3-cephem-4-carboxylate (If)

The general procedure of Example 1 was repeated except that the trimethylamine utilized therein was replaced by an equimolar amount of N,N-dimethylethylamine. The crude product had a $\Delta^2$:$\Delta^3$ ratio of 1:1. After purification the title compound was obtained in 15% yield and decomposed above 150° C. Estimated purity 77%.

EXAMPLE 7

7-[(Z)-2-(2-Aminothiazol-4-yl)-2-methoxyiminoacetamido]-3-(N,N-diethyl-N-methylammonium)methyl-3-cephem-4-carboxylate (Ig)

The general procedure of Example 1 was repeated except that the trimethylamine utilized therein was replaced by an equimolar amount of diethylmethylamine. The crude product had a $\Delta^2$:$\Delta^3$ ratio of 1:1. After purification the title compound was obtained in 10% yield and decomposed above 150° C. Estimated purity 65%.

EXAMPLE 8

7-[(Z)-2-(2-Aminothiazol-4-yl)-2-ethoxyiminoacetamido]-3-(trimethylammonium)methyl-3-cephem-4-carboxylate (Ih)

The general procedure of Example 1 was repeated except that the benzhydryl 3-iodomethyl-7-[(Z)-2-methoxyimino-2-(2-tritylaminothiazol-4-yl)acetamido]-3-cephem-4-carboxylate (VIIa) was replaced by an equimolar amount of the corresponding ethoxyimino compound (VIIb) (prepared in Preparation No. 8). The crude product had a $\Delta^2$:$\Delta^3$ ratio of 3:1. After purification the title compound was obtained in 3% yield and decomposed above 150° C. Estimated purity 70%.

Spectral Data for the Compounds of Examples 2–8

(a) Infrared Spectra (KBr)

All of the products gave similar infrared spectra: 1770–1775 cm$^{-1}$ ($\beta$-lactam C=O), 1660 cm$^{-1}$ (CONH), 1610 cm$^{-1}$ (COO$^-$).

(b) Ultraviolet Spectra (1/15M phosphate buffer; pH 7)

All of the products except that of Example 4 showed similar spectra: 235 nM ($\epsilon$ 15700–16400), 257 nM ($\epsilon$ 15400–16000). The compound of Example 4 showed: 235 nM ($\epsilon$ 17600), 255 nM ($\epsilon$ 18600, sh), 260 nM ($\epsilon$ 19000), 266 nM ($\epsilon$ 17900, sh).

(c) NMR Spectra (D$_2$O)

| Compound of Example | N$^+$—CH$_3$ (s) | O—CH$_3$ (3H, s) | 6-H (1H, d, 4–5Hz) | 7-H (1H, d, 4–5Hz) | thiazole-H (1H, s) | others |
|---|---|---|---|---|---|---|
| 2 | 3.20 (3H) 3.25 (3H) | 4.10 | 5.46 | 5.90 | 7.10 | |
| 3 | 3.08 (3H) 3.15 (3H) | 4.10 | 5.46 | | 7.10 | 5.6–6.4 (4H, m, 7-H, CH=CH$_2$) |
| 4 | 3.04 (3H) 3.21 (3H) | 4.09 | 5.45 | 5.94 | 7.06 | 4.75 (2H, s, PyrCH$_2$) 7.66 (1H, d-d, 8 & 4Hz, Pyr-H) 8.12 (1H, d, 8Hz, Pyr-H) 8.74 (2H, s, Pyr-H) |
| 5 | 3.18 (3H) 3.25 (3H) | 4.10 | 5.45 | 5.90 | 7.10 | 2.50 (6H, s, N(CH$_3$)$_2$) |
| 6 | 3.10 (3H) 3.15 (3H) | 4.10 | 5.45 | 5.90 | 7.10 | 1.48 (3H, t 7Hz, CH$_2$CH$_3$) |
| 7 | 3.05 (3H) | 4.10 | 5.44 | 5.95 | 7.10 | 1.45 (6H, t, 7Hz, CH$_2$CH$_3$) |
| 8 | 3.25 (9H) | — | 5.50 | 5.97 | 7.10 | 1.45 (3H, t 7Hz, CH$_2$CH$_3$) |

It has been found that both the $\Delta^2$:$\Delta^3$ ratio and the yield of product may be improved if the filtrate from the originally precipitated quaternary salt (XV) is allowed to stand for a brief period and refiltered through the bed of originally recovered Compound XV, particularly if this refiltration step is repeated several times. The yield can also be increased somewhat if a small amount of the original tertiary amine reactant is added to this filtrate. This is shown in the following example, which is a variation of Example 1.

EXAMPLE 9

7-[(Z)-2-(2-Aminothiazol-4-yl)-2-methoxyiminoacetamido]-3-(trimethylammonium)methyl-3-cephem-4-carboxylate (Ia)

A solution of trimethylamine (1M solution in ether, 10 mL) was added in one portion to a stirred solution of the iodide Compound VIIa (4.68 g, 5 mmoles) in ether (500 mL). The mixture was stirred for 10 minutes and the precipitated quaternary salt (XVa) was collected by filtration and washed with a small amount of ether. The filtrate and the washings were combined and allowed to stand at room temperature for another 10 minutes, and the second precipitate which separated was collected by filtration on the same funnel on which the first precipitate was kept as a bed. The filtrate was filtered three times in the same manner at 10 minute intervals to afford the quaternary salt (XVa) (3.58 g, 72% from VIIa). To the final filtrate was added a solution of trimethylamine (1M solution in ether, 2 mL) and the same refiltering operation was repeated three additional times at 10 minute intervals to give additional XVa (0.56 g, 11%). To the resulting filtrate was added additional 1M trimethylamine solution (1 mL) and the refiltering operation was repeated twice again at 10 minute intervals to give the third crop of XVa (0.134 g, 2.7%). The total yield of XVa was 4.27 g (86%).

A mixture of XVa (4.20 g, 4.22 mmoles), anisole (1 mL) and TFA (40 mL) was stirred for 1.5 hours at room temperature. The mixture was evaporated under reduced pressure below 20° C. and the dark residue was triturated with isopropyl ether (300 mL) to precipitate the TFA salt (3.50 g), which was collected by filtration and dried under reduced pressure. The TFA salt was dissolved in methanol (50 mL), treated with a small amount of charcoal and filtered. The filtrate was concentrated under reduced pressure and sodium 2-ethylhexanoate (1M solution in ethyl acetate, 15 mL) was added to the concentrate. The mixture was diluted with ethyl acetate (300 mL) to precipitate the crude title product (2.36 g, estimated purity 50%), which was collected by filtration, washed with a small amount of ethyl acetate and dried. The ratio of $\Delta^2$ isomer to $\Delta^3$ isomer of the crude product was 1:4 (HPLC, Lichrosorb RP-18; mobile phase, 1/100M ammonium phosphate buffer, pH 7—CH$_3$OH, 90:10; Retention time, $\Delta^2$ isomer 6' 54", $\Delta^3$ isomer 8' 29").

The crude product (2.36 g) was dissolved in a small amount of water and purified using HPLC (Waters Associates, System 500, PrepPAK 500/C$_{18}$; mobile phase, 7% methanol). The HPLC eluate containing the product was concentrated under reduced pressure below 35° C. and the concentrate was freeze-dried to give the title compound. Yield 959 mg (42%, based on the iodide VIIa). Amorphous powder. Estimated purity 80% (by HPLC). The ratio of $\Delta^2$ isomer to $\Delta^3$ isomer was 1:17. It was gradually decomposed above 160° C.

We claim:

1. A compound of the formula

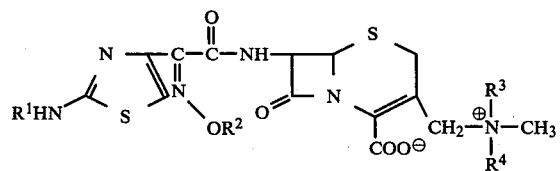

wherein $R^1$ is hydrogen or a conventional amino-protecting group, $R^2$ and $R^3$ each are independently methyl or ethyl, and $R^4$ is methyl, ethyl, n-propyl, isopropyl, n-butyl, isobutyl, allyl, 2-butenyl, 3-butenyl, 2-hydroxyethyl, 3-hydroxypropyl, 2-(dimethylamino)ethyl, pyridylmethyl, pyridylethyl, benzyl or phenethyl, or a nontoxic pharmaceutically acceptable acid addition salt or solvate thereof.

2. A compound of claim 1 wherein $R^1$ is hydrogen, $R^2$ is methyl, $R^3$ is methyl or ethyl and $R^4$ is methyl, ethyl, 2-hydroxyethyl, 2-(dimethylamino)ethyl, allyl or pyridylmethyl, or a nontoxic pharmaceutically acceptable acid addition salt or solvate thereof.

3. The compound of claim 1 which is 7-[(Z)-2-(2-aminothiazol-4-yl)-2-methoxyiminoacetamido]-3-(trimethylammonium)methyl-3-cephem-4-carboxylate, or a nontoxic pharmaceutically acceptable acid addition salt or solvate thereof.

4. The compound of claim 1 which is 7-[(Z)-2-(2-aminothiazol-4-yl)-2-methoxyiminoacetamido]-3-[N,N-dimethyl-N-(2-hydroxyethyl)ammonium]methyl-3-cephem-4-carboxylate, or a nontoxic pharmaceutically acceptable acid addition salt or solvate thereof.

5. The compound of claim 1 which is 7-[(Z)-2-(2-aminothiazol-4-yl)-2-methoxyiminoacetamido]-3-(N,N-dimethyl-N-allylammonium)methyl-3-cephem-4-carboxylate, or a nontoxic pharmaceutically acceptable acid addition salt or solvate thereof.

6. A method of combatting bacterial infection in a warm-blooded mammal in need of such treatment comprising administering to said warm-blooded mammal an antibacterially effective amount of at least one compound of claim 1.

7. The method of claim 6 wherein the compound of claim 1 is 7-[(Z)-2-(2-aminothiazol-4-yl)-2-methoxyiminoacetamido]-3-(trimethylammonium)methyl-3-cephem-4-carboxylate, or a nontoxic pharmaceutically acceptable acid addition salt or solvate thereof.

8. An antibacterial composition comprising an antibacterially effective amount of at least one compound of claim 1 and an inert pharmaceutical carrier.

9. The composition of claim 8 wherein the compound of claim 1 is 7-[(Z)-2-(2-aminothiazol-4-yl)-2-methoxyiminoacetamido]-3-(trimethylammonium)methyl-3-cephem-4-carboxylate, or a nontoxic pharmaceutically acceptable acid addition salt or solvate thereof.

10. An antibacterial composition in unit dosage form comprising from about 50 mg to about 1500 mg of at least one compound of claim 1 and an inert pharmaceutical carrier.

11. The composition of claim 10 wherein the compound of claim 1 is 7-[(Z)-2-(2-aminothiazol-4-yl)-2-methoxyiminoacetamido]-3-(trimethylammonium)-methyl-3-cephem-4-carboxylate, or a nontoxic pharmaceutically acceptable acid addition salt or solvate thereof.

* * * * *